US00PP35044P2

(12) United States Plant Patent
Clark

(10) Patent No.: US PP35,044 P2
(45) Date of Patent: Mar. 14, 2023

(54) ***COLEUS* PLANT NAMED 'UF19-82-2'**

(50) Latin Name: *Coleus scutellarioides*
Varietal Denomination: UF19-82-2

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 17 days.

(21) Appl. No.: 17/803,404

(22) Filed: Jun. 24, 2022

(51) Int. Cl.
*A01H 5/12* (2018.01)
*A01H 6/50* (2018.01)

(52) U.S. Cl.
USPC ..... Plt./469

(58) Field of Classification Search
USPC ..... Plt./469, 373, 263.1
CPC ... A01H 5/12; A01H 5/00; A01H 5/02; A01H 6/50
See application file for complete search history.

(56) References Cited

U.S. PATENT DOCUMENTS

PP25,650 P3 6/2015 Clark et al.

*Primary Examiner* — June Hwu
(74) *Attorney, Agent, or Firm* — Katherine Koenig; Koenig IP Works, PLLC

(57) ABSTRACT

A new and distinct cultivar of *Coleus* (*Coleus scutellarioides*) plant named 'UF19-82-2', selected for having a combination of desirable traits that make it well-suited for superior performance as an annual plant in the summer landscape. 'UF19-82-2' has foliage that is consistent dark crimson red with numerously lobed and well-defined yellow green margins across the plant in both sun and shade trial conditions. 'UF19-82-2' is novel due to its extremely vigorous upright and spreading growth habit and consistent color in both mature and immature foliage.

3 Drawing Sheets

Genus and species: *Coleus scutellarioides*.
Cultivar Denomination: 'UF19-82-2'.

CROSS-REFERENCE TO RELATED APPLICATIONS

N/A.

ACKNOWLEDGEMENT OF FEDERAL RESEARCH SUPPORT

N/A.

BACKGROUND OF THE NEW CULTIVAR

The present disclosure relates to a new and distinct cultivar of *Coleus* plant named 'UF19-82-2'. The new cultivar 'UF19-82-2' originated from an open pollination conducted in May-November 2018 in Gainesville, Fla. between the female *Coleus* plant 'UF18-72-2' (unpatented) and an unknown male *Coleus* plant. A single seedling was chosen in May 2019 for further asexual propagation in Gainesville, Fla.

The new cultivar 'UF19-82-2' has been reproduced asexually for over 18 months through vegetative meristem tip cuttings and has been found to retain its distinctive characteristics through successive asexual propagations. 'UF19-82-2' was first propagated asexually by vegetative meristem tip cuttings in May 2019 in Gainesville, Fla., and has remained true-to-type since that time.

Plant Breeder's Rights for the new cultivar 'UF19-82-2' have not been applied for, and 'UF19-82-2' has not been made publicly available more than one year prior to the filing date of this application.

When compared to the female parent 'UF18-72-2', the new cultivar 'UF19-82-2' has a vigorous upright and spreading habit, that grows more horizontal than vertical, and is well-branched. Leaves across the entire plant are predominantly dark crimson red, with very well-defined yellow green margins. Additionally, 'UF19-82-2' has leaves with margins having numerous lobes. In contrast, the female parent 'UF18-72-2' is much less vigorous and is more upright in habit with less lateral branching. Additionally, 'UF18-72-2' has leaves with fewer lobes and leaves that are colored maroon with irregular lime green margins.

The new cultivar 'UF19-82-2' was selected mainly for its superb vigor, contrasting foliage colors, and unique leaf shape when grown under a variety of environmental conditions. 'UF19-82-2' is a uniquely novel plant in that it has foliage that is dark crimson red with a consistent yellow green margins. These contrasting colors are particularly novel on a leaf with a margin having numerous lobes, when present on a plant that is wider than it is tall.

SUMMARY OF THE INVENTION

The new cultivar 'UF19-82-2' has not been observed under all possible environmental conditions. The phenotype of the new cultivar may vary with variations in environment and cultural practices such as temperature, light intensity, fertilization, irrigation, and application of plant growth regulators without any change in genotype.

The following are the most outstanding and distinguishing characteristics of 'UF19-82-2' when grown under normal horticultural practices in Gainesville, Fla. 'UF19-82-2' is exceptionally vigorous with an upright and spreading growth habit and excellent heat tolerance. It produces consistent dark crimson red leaves with well-defined yellow green margins that are significantly different than other *Coleus* plants because they include numerous lobes. It has superior stability in foliage color in both sun and shade conditions, maintaining stable color in all conditions. It has excellent lateral branching, making it suitable for propagators and producers, and it has been observed to have long-season performance in landscape trials in Gainesville, Fla.

DESCRIPTION OF THE FIGURES

This new *Coleus* cultivar 'UF19-82-2' is illustrated by the accompanying photographs, which show the plant's form and foliage. The colors shown are as true as can be reasonably obtained by conventional photographic procedures.

FIG. 2 shows the growth habit, form, and foliage of the claimed plant; and

FIG. 3 shows a close-up view of the foliage of the claimed plant.

DETAILED BOTANICAL DESCRIPTION OF THE CULTIVAR

Figure 1:
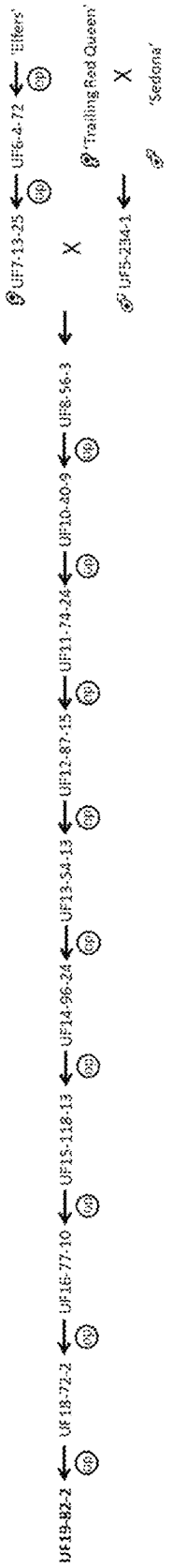
FIG. 1 shows the pedigree of the claimed plant.
Figure 2:
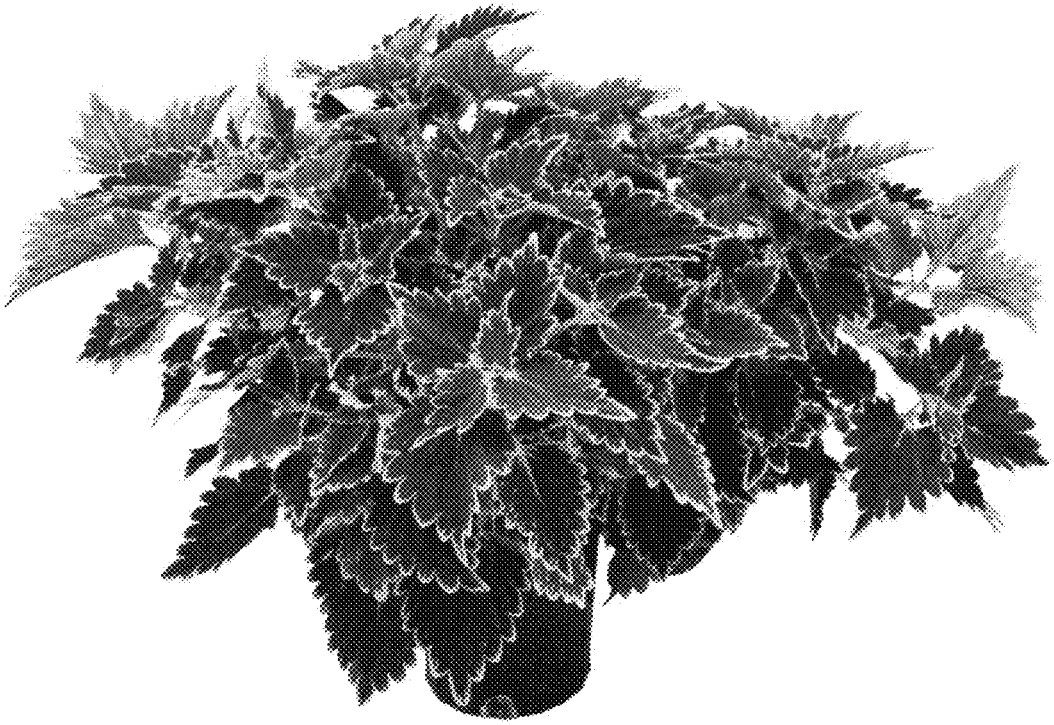
FIGS. 2 and 3 were taken from plants grown nine weeks from unrooted cuttings in September-November 2021 in a glass-covered greenhouse in Gainesville, Fla.
Figure 3:
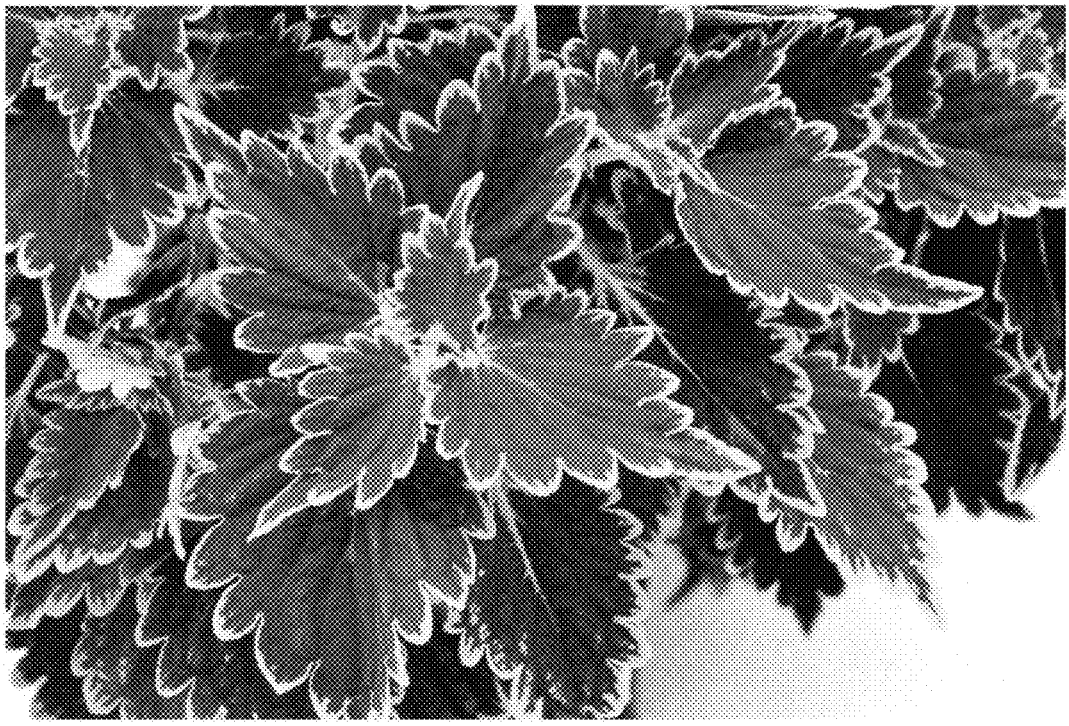

The following detailed description sets forth the distinctive characteristics of the new cultivar 'UF19-82-2'. Color references are to The R.H.S. Colour Chart of The Royal Horticultural Society of London (R.H.S.), 2007 (5th Edition).

DESCRIPTION OF GROWING CONDITIONS

The detailed description was generated using nine-week-old plants of the new cultivar 'UF19-82-2' grown from unrooted cuttings in September-November 2021 in a glass-covered greenhouse in Gainesville, Fla. The plants were propagated in mist for ten days after cuttings were stuck, then grown in one-gallon pots for approximately seven and a half additional weeks.

BOTANICAL DESCRIPTION

Botanical classification:
- *Family*.—Lamiaceae.
- *Botanical name*.—*Coleus scutellarioides*.
- *Common name*.—*Coleus*.
- *Cultivar*.—'UF19-82-2'.

Parentage:
- *Female or seed parent*.—'UF18-72-2'.
- *Male or pollen parent*.—Unknown.

Plant description:
- *Growth habit*.—Upright and spreading.
- *Plant height* (*from top of soil*).—45-50 cm.

Plant width (horizontal plant diameter): 75-85 cm.

Propagation:
- *Type*.—Vegetative meristem tip cuttings having at least 1 node.
- *Time to initiate roots*.—3-4 days.
- *Time to produce a rooted cutting*.—7-10 days.

Roots:
- *Rooting habit*.—Fibrous.
- *Root description*.—Callus forms in 2-3 days, roots initiate in 3-4 days and become a highly branched cutting in 7-10 days.

Branches:
- *Quantity per plant*.—7-8.
- *Branch color*.—RHS 143B (strong yellow green).
- *Texture*.—Smooth.
- *Pubescence*.—Not present.
- *Stem description*.—Square-shaped stem, 1.2 cm in diameter at the soil line.
- *Branch diameter*.—0.8-0.9 cm at the base of a 40 cm long branch.
- *Branch length*.—38-40 cm.
- *Internode length*.—3-4 cm.
- *Anthocyanin*.—Not present.

Foliage description:
- *Quantity of leaves per branch*.—26-28.
- *Arrangement*.—Opposite.
- *Fragrance*.—Not fragrant.
- *Shape*.—Ovate.
- *Length*.—12-13 cm.
- *Width*.—11-12 cm.
- *Apex*.—Broadly acuminate.
- *Base*.—Attenuate.
- *Margin*.—Lobed, medium depth.
- *Leaf texture*.—Top: Pulverulent. Bottom: Smooth.
- Pubescence: Not present.
- *Venation color*.—Upper surface, base: RHS 143C (strong yellow green). Upper surface, rest of leaf: RHS N186B (dark greyish purple). Lower surface: RHS 143D (moderate yellow green).
- *Venation pattern*.—Upper surface: Reticulate. Lower surface: Reticulate.
- *Color, immature leaf*.—Upper surface, base/main: RHS 183A (dark red). Upper surface, margins: RHS 143B (strong yellow green). Lower surface, base/main: RHS 138A (moderate yellowish green) with irregular patterns of RHS 187A (dark crimson red).
- *Color, mature leaf*.—Upper surface, base/main: RHS 187A (dark crimson red). Upper surface, margins: RHS 143B (strong yellow green). Lower surface, base/main: RHS 138A (moderate yellowish green) with irregular patterns of RHS 187A (dark crimson red).
- *Petiole length*.—5-6 cm.
- *Petiole diameter*.—0.3-0.4 cm.
- *Petiole color*.—RHS 143B (strong yellow green).
- *Petiole texture*.—Smooth, no pubescence.

Flowers and seeds: Flowers and seeds have not been observed.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Fla. have been long-tailed or citrus mealybugs (*Pseudococcus* sp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Peronon-*

*spora lamii*). This pathogen has been observed in stock materials grown closely together in cooler growing seasons.

COMPARISON WITH KNOWN CULTIVARS

Plants of the new *Coleus* cultivar 'UF19-82-2' can be compared to those of 'UF12-87-9' (sold commercially under the trade name MAIN STREET OXFORD STREET™, U.S. Plant Pat. No. 25,650). The main base color on the upper surface of mature leaves of 'UF19-82-2' is RHS 187A (dark crimson red). In contrast, the main base color on the upper surface of mature leaves of 'UF12-87-9' is RHS 185A (deep red). Additionally, 'UF19-82-2' has leaf margins that are more deeply lobed than the leaf margins of 'UF12-87-9'.

What is claimed is:

1. A new and distinct *Coleus scutellarioides* plant named 'UF19-82-2' as illustrated and described herein.

* * * * *